US012558205B2

(12) United States Patent
Park

(10) Patent No.: US 12,558,205 B2
(45) Date of Patent: Feb. 24, 2026

(54) COMPOSITION FOR FORMING ARTIFICIAL TOOTH, METHOD OF PREPARING ARTIFICIAL TOOTH, AND ARTIFICIAL TOOTH PREPARED THEREBY

(71) Applicant: ODS CO., LTD., Incheon (KR)

(72) Inventor: Sung Won Park, Incheon (KR)

(73) Assignee: ODS CO., LTD., Incheon (KR)

(*) Notice: Subject to any disclaimer, the term of this patent is extended or adjusted under 35 U.S.C. 154(b) by 636 days.

(21) Appl. No.: 18/013,547

(22) PCT Filed: Aug. 26, 2021

(86) PCT No.: PCT/KR2021/011440
§ 371 (c)(1),
(2) Date: Dec. 29, 2022

(87) PCT Pub. No.: WO2022/045794
PCT Pub. Date: Mar. 3, 2022

(65) Prior Publication Data
US 2023/0293276 A1 Sep. 21, 2023

(30) Foreign Application Priority Data
Aug. 26, 2020 (KR) ........................ 10-2020-0107964

(51) Int. Cl.
*B33Y 70/00* (2020.01)
*A61C 13/00* (2006.01)
(Continued)

(52) U.S. Cl.
CPC ........ *A61C 13/082* (2013.01); *A61C 13/0019* (2013.01); *A61K 6/62* (2020.01); *A61K 6/831* (2020.01); *B33Y 70/00* (2014.12)

(58) Field of Classification Search
CPC ....... A61K 6/887; C08L 33/10; C08F 265/06; C08F 222/1065; C08F 222/1025; C08F 220/20; C08F 222/102
See application file for complete search history.

(56) References Cited

U.S. PATENT DOCUMENTS 10,709,530 B2 * 7/2020 Gomi ................. A61C 13/1003
2021/0238339 A1 * 8/2021 Govindarajan ....... G03F 7/0037

FOREIGN PATENT DOCUMENTS

JP 6271772 B2 1/2018
KR 10-2011-0041682 A 4/2011
(Continued)

*Primary Examiner* — Peter A Salamon
(74) *Attorney, Agent, or Firm* — You & IP, LLC

(57) ABSTRACT

A composition for forming artificial teeth, a method for producing artificial teeth, and artificial teeth produced using the technique are disclosed. The disclosed composition for forming artificial teeth includes 100 parts by weight of a first photocurable compound illustrated in Chemical Formula 1 below, 5 to 20 parts by weight of a second photocurable compound represented by Chemical Formula 2 below, 25 to 50 parts by weight of a third photocurable compound depicted by Chemical Formula 3 below, and 1 to 10 parts by weight of a fourth photocurable compound shown by Chemical Formula 4 below.

[Chemical Formula 1]

$R'CH_2[C(CH_3)(R)CH_2]_2R'$ ($R$ = H or $CH_3$, $R'{=}NHCO_2CH_2CH_2O_2CC(CH_3){=}CH_2$)

[Chemical Formula 2]

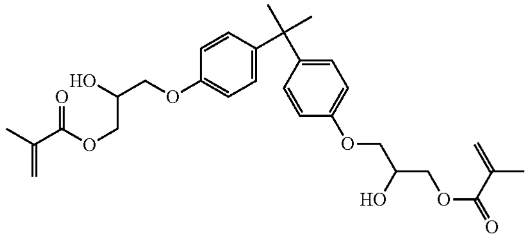

[Chemical Formula 3]

$CH_2{=}C(CH_3)COOCH_2CH_2OH$

[Chemical Formula 4]

$CH_2{=}C(CH_3)COO(CH_2CH_2O)_3COC(CH_3){=}CH_2$.

11 Claims, 1 Drawing Sheet

(51) Int. Cl.

| | |
|---|---|
| ***A61C 13/08*** | (2006.01) |
| ***A61K 6/62*** | (2020.01) |
| ***A61K 6/831*** | (2020.01) |

(56) References Cited

FOREIGN PATENT DOCUMENTS

| | | | | | |
|---|---|---|---|---|---|
| KR | 10-1630625 | B1 | | 6/2016 | |
| KR | 10-2020131 | B1 | | 9/2019 | |
| KR | 102041603 | B1 | * | 11/2019 | ............... A61K 6/04 |
| KR | 10-2130780 | B1 | | 7/2020 | |

* cited by examiner

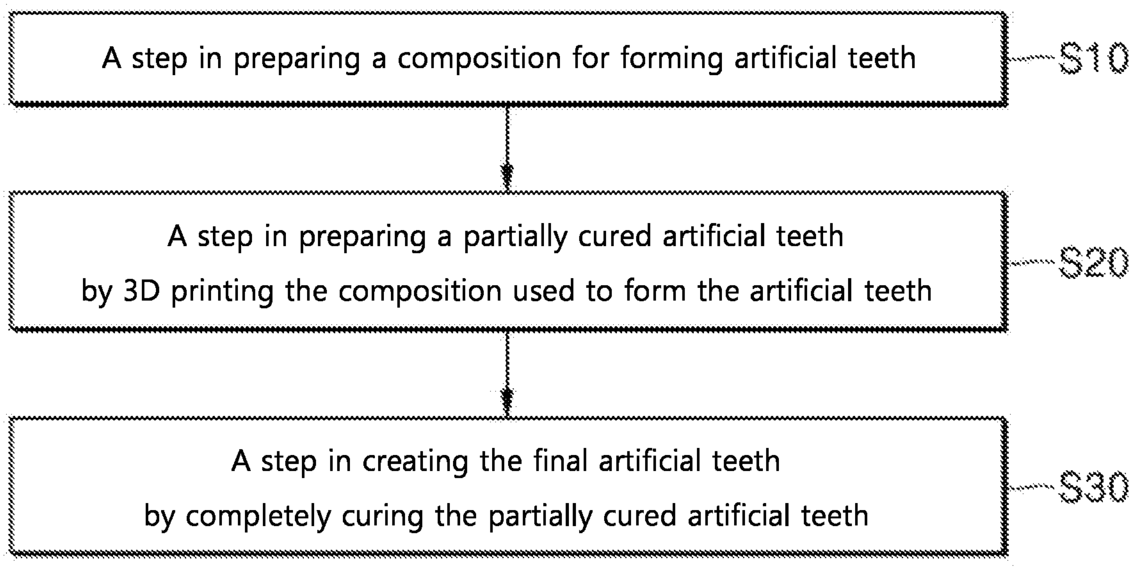
A step in preparing a composition for forming artificial teeth
S10
A step in preparing a partially cured artificial teeth by 3D printing the composition used to form the artificial teeth
S20
A step in creating the final artificial teeth by completely curing the partially cured artificial teeth
S30

COMPOSITION FOR FORMING ARTIFICIAL TOOTH, METHOD OF PREPARING ARTIFICIAL TOOTH, AND ARTIFICIAL TOOTH PREPARED THEREBY

TECHNICAL FIELD

A composition for forming artificial teeth, a method for preparing the artificial teeth, and the artificial teeth produced using the technique are disclosed. Specifically, a composition capable of producing artificial teeth with greater strength that do not break easily, a method for preparing the artificial teeth, and the artificial teeth manufactured by the method are described.

BACKGROUND TECHNOLOGY

Metal crowns employing a metal such as gold, porcelain fused metal (PFM) in which a porcelain artificial crown is laminated on the surface of a metal skeleton, zirconia created by cutting raw zirconium oxide stone, and resin-based artificial teeth are examples of artificial teeth.

However, metal crowns are not only aesthetically unappealing but in the case of gold crowns, there is an issue with increasing production costs due to the rising price of gold. Because the tensile strength of porcelain is lower than that of real teeth, occlusal pressure can cause the porcelain in PFM crowns made of porcelain to split or break. Since the tensile strength of zirconium oxide is greater than that of natural teeth, normal teeth combined with implanted artificial teeth can be fractured or shattered as a result of occlusal pressure.

Publication No. 10-2011-0041682 of the Korean Patent Office describes a technique for producing a zirconia tooth in which the whole tooth is molded from zirconia. However, this technique is solely concerned with cosmetic aspects, and because artificial teeth are made from zirconia, which has a higher tensile strength than real teeth, the natural teeth may be damaged by occlusal pressure after implantation.

SUMMARY OF THE INVENTION

Technical Problem

One embodiment of the present invention provides a composition for forming artificial teeth that are capable of producing artificial teeth with high strength and resistance to breakage.

Another aspect of the present invention provides a method for producing artificial teeth that includes preparing the compound for creating the artificial teeth.

A further aspect of the present invention offers artificial teeth made using the artificial teeth production process.

Technical Solution

The present invention provides the following information: 100 parts by weight of the first photocurable compound shown below in Chemical Formula 1; 5 to 20 parts by weight of a second photocurable compound specified below in Chemical Formula 2; 25 to 50 parts by weight of a third photocurable compound depicted in the following Chemical Formula 3; and a composition for fabricating artificial teeth having 1 to 10 parts by weight of a fourth photocurable compound illustrated in Chemical Formula 4 below.

[Chemical Formula 1]

$R'CH_2[C(CH_3)(R)CH_2]_2CH_2R'[R{=}H$ or $CH_3$, $R'{=}NHCO_2CH_2CH_2O_2CC(CH_3){=}CH_2]$

[Chemical Formula 2]

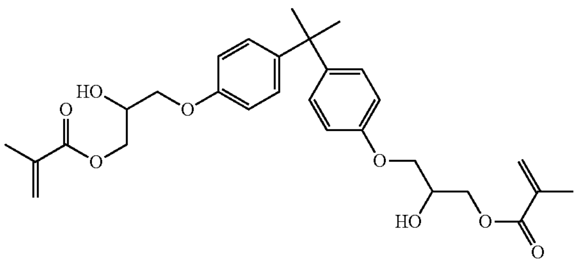

[Chemical Formula 3]

$CH_2{=}C(CH_3)COOCH_2CH_2OH$

The composition for forming artificial teeth may also include between 0.5 and 5 parts by weight of an acrylic resin, based on 100 parts by weight of the total weight of the first photocurable compound, the second photocurable compound, the third photocurable compound, and the fourth photocurable compound.

The composition for forming artificial teeth may also include between 1 to 20 parts by weight of a photoinitiator based on 100 parts by weight of the total weight of the first photocurable compound, the second photocurable compound, the third photocurable compound, and the fourth photocurable compound.

The composition for forming artificial teeth may also include between 0.1 to 2 parts by weight of an antioxidant based on 100 parts by weight of the total weight of the first photocurable compound, the second photocurable compound, the third photocurable compound, and the fourth photocurable compound.

The composition for forming artificial teeth may also include between 0.1 to 10 parts by weight of a white pigment and 0.001 to 0.15 parts by weight of a colored pigment, based on 100 parts by weight of the total weight of the first photocurable compound, the second photocurable compound, the third photocurable compound, and the fourth photocurable compound.

The color pigment may also include between 0.0005 to 0.075 parts by weight of yellow pigment and 0.0005 to 0.075 parts by weight of orange pigment, based on 100 parts by weight of the total weight of the first photocurable compound, the second photocurable compound, the third photocurable compound, and the fourth photocurable compound.

By combining a red pigment with a yellow pigment in a weight ratio of 2:8, the aforementioned orange pigment can be created.

The composition used to create prosthetic teeth may not include a solvent.

The composition used to create artificial teeth can have a viscosity between 300 and 800 cps.

The artificial tooth-forming component may be liquid, photocurable, and 3D-printable.

This invention further provides the following steps for the production of artificial teeth: preparing a mixture for artificial teeth formation (S10); manufacturing a partly cured artificial tooth by 3D printing an artificial tooth component (S20); and creating the final artificial tooth by curing the partly treated artificial tooth to completion (S30).

Another aspect of the present invention is providing artificial teeth made using the production method described above. The artificial teeth may be opaque or translucent.

Effects of the Invention

A composition for forming artificial teeth in accordance with one embodiment of the present invention can produce artificial teeth with exceptional strength and resistance to damage, and a surface that does not harm natural teeth.

BRIEF DESCRIPTION OF THE DRAWINGS

FIG. 1 depicts a technique for producing artificial teeth in accordance with one embodiment of the present invention.

SPECIFIC INSTRUCTIONS FOR IMPLEMENTING THE INVENTION

The following is a detailed description of a composition for producing artificial teeth in accordance with one embodiment of the present invention.

The composition for forming artificial teeth in accordance with one embodiment of the present invention includes the following: 100 parts by weight of the first photocurable compound represented by Chemical Formula 1 below; 5 to 20 parts by weight of the second photocurable compound shown in Chemical Formula 2 below; 25 to 50 parts by weight of the third photocurable compound depicted in Chemical Formula 3 below; and 1 to 10 parts by weight of the fourth photocurable compound represented by Chemical Formula 4 below.

[Chemical Formula 1]

$R'CH_2[C(CH_3)(R)CH_2]_2CH_2R'[R{=}H$ or $CH_3,\ R'{=}NHCO_2CH_2CH_2O_2CC(CH_3){=}CH_2]$

[Chemical Formula 2]

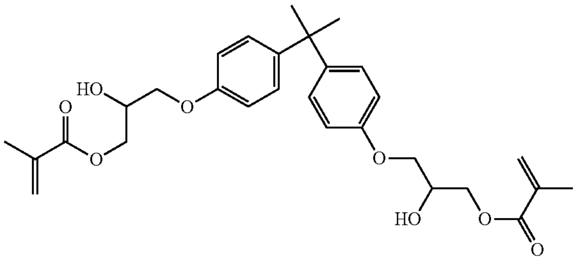

[Chemical Formula 3]

$CH_2{=}C(CH_3)COOCH_2CH_2OH$

[Chemical Formula 4]

$CH_2{=}C(CH_3)COO(CH_2CH_2O)_3COC(CH_3){=}CH_2$

The first photocurable compound may consist of a combination of isomers of R=H and R=CH3 in a prescribed ratio. For instance, the molecular weight of the first photocurable molecule may be C23H38N2O8 and a molecular weight of 470.56.

When the contents of the first photocurable compound, the second photocurable compound, the third photocurable compound, and the fourth photocurable compound are within the above range, respectively, it has superb flexural strength and an appropriate level of the flexural modulus of elasticity, therefore it is not readily broken. Because the majority of them are composed of resin and have a smooth surface, it is possible to create artificial teeth that do not harm natural teeth.

Each of the photocurable compounds may be (ultraviolet) indurative.

In addition, the composition for forming artificial teeth may comprise between 0.5 and 5 parts by weight of an acrylic resin per 100 parts by weight of the total weight of the first photocurable compound, the second photocurable compound, the third photocurable compound, and the fourth photocurable compound. When the acrylic resin content falls within the aforementioned range, the artificial teeth' overall physical qualities (e.g., attributes other than flexural strength and modulus of elasticity) may be enhanced.

The acrylic resin may include the following or a combination thereof: Dianal BR-83 (manufactured by Mitsubishi Rayon, glass transition temperature 105° C., weight-average molecular weight 40,000); Dianal BR-87 (manufactured by Mitsubishi Rayon, glass transition temperature 105° C., weight-average molecular weight 25,000); Dianal BR-60 (manufactured by Mitsubishi Rayon, glass transition temperature 75 C, weight-average molecular weight 70,000); and Dianal BR-77 (manufactured by Mitsubishi Rayon, glass transition temperature 80 C, weight-average molecular weight 65,000).

The composition for forming artificial teeth may also contain 1 to 20 parts by weight of a photoinitiator per 100 parts by weight of the total weight of the first photocurable compound, the second photocurable compound, the third photocurable compound, and the fourth photocurable compound. When the photoinitiator concentration falls within the aforementioned range, the curing time of the composition for creating artificial teeth is optimal and the storage stability can be enhanced. The surface of the cured product can be achieved without wrinkles for a smooth finish (i.e., the final artificial teeth).

The photoinitiator may include the following or a combination of the following substances: Acetophenone, benzyl, benzoin, benzophenone, 2-benzoyl benzoic acid, 4,4'-bis (diethylamino)benzophenone, 4,4'-bis(dimethylamino)benzophenone, benzoin methyl ether, benzoin isopropyl ether, benzoin isobutyl ether, benzoin ethyl ether, 4-benzoyl benzoic acid, 2,2'-bis(2-chlorophenyl)-4,4,5,5'-tetraphenyl-1,2'-biimidazole, methyl 2-benzoyl benzoate, 2-(1,3-benzodioxol-5-yl)-4,6-bis(trichloromethyl)-1,3,5-triazine, 2-benzyl-2-(dimethylamino)-4'-morpholinobutyrophenone, (±)-camphorquinone, 2-chlorothioxanthone, 4,4'-dichlorobenzophenone, 2,2-diethoxy Acetophenone, 2,2-dimethoxy-2-phenyl acetophenone, 2,4-diethyl thioxanthene-9-one, diphenyl(2,4,6-trimethyl benzoyl)phosphine oxide, 1,4-dibenzoylbenzene, 2-ethyl anthraquinone, 1-hydroxy cyclohexyl phenyl ketone, 2-hydroxy-2-methylpropiophenone, 2-hydroxy-4'-(2-hydroxyethyl)-2-methylpropiophenone, 2-isopropyl thioxanthone lithium phenyl (2,4,6-trimethyl benzoyl) phosphinate, 2-methyl-4'-(methylthio)-2-morpholinopropiophenone, 2-isonitrosopropiophenone, 2-phenyl-2-(p-toluenesulfonyloxy)acetophenone, and phenyl bis(2,4,6-trimethyl benzoyl) phosphine oxide.

Moreover, the composition for forming artificial teeth may additionally include antioxidant 0.1 to 2 parts by weight per 100 parts by weight of the total weight of the first photocurable compound, the second photocurable compound, the third photocurable compound, and the fourth photocurable compound. When the antioxidant concentration falls within the specified range, a sufficient antioxidant effect can be attained without impairing the artificial teeth's other physical qualities.

The antioxidant may include the following or a combination of the following substances: hindered phenolic compounds such as 2,6-di-tert-butyl-para-cresol and 4,4'-methylenebis (6-tert-butyl-ortho-cresol); aromatic amine-based compounds such as dioctyl diphenylamine and phenyl alpha naphthalene; sulfur compounds; phosphorus compounds; dibutyl dithiophosphate that is sulfur and phosphorus compounds (e.g., sulfurized fats, dimethyl sulfide, dibenzyl disulfide, alkyldithiophosphates); and disalicylidine diamino propane; didodecylthiobenzimidazole.

In addition, the composition for forming artificial teeth may further include 0.1 to 10 parts by weight of a white pigment and 0.001 to 0.15 parts by weight of a colored pigment per 100 parts by weight of the total weight of the first photocurable compound, the second photocurable compound, the third photocurable compound, and the fourth photocurable compound.

The white pigment may be composed of rutile, titanium dioxide, zinc oxide, zinc sulfide, lithopone, lead white, antimony oxide, or a mixture of these substances.

The typical particle diameter of the white pigment may range from 20 to 80 nm (e.g., 40 to 60 nm). For example, the white pigment may contain rutile with a particle diameter of 50 nm on average.

When the average particle diameter of the white pigment falls within the aforementioned range (20 to 80 nm), the dispersibility of the white pigment is enhanced in the composition for forming artificial teeth, thereby increasing not only the storage stability but also the transparency of the final artificial teeth.

The colored pigment may include a yellow pigment and an orange pigment.

Based on 100 parts by weight of the total weight of the first photocurable compound, the second photocurable compound, the third photocurable compound, and the fourth photocurable compound, the yellow pigment concentration may range from 0.0005 to 0.075 parts by weight.

The orange pigment concentration may range from 0.0005 to 0.075 parts by weight per 100 parts by weight of the total weight of the first photocurable compound, the second photocurable compound, the third photocurable compound, and the fourth photocurable compound.

Mixing a red pigment and a yellow pigment in a weight ratio of 2:8 yields an orange pigment. Thus, the orange pigment may be created by combining two parts by the weight of red pigment and eight parts by the weight of yellow pigment.

The yellow pigment may include the following colors or a combination of the following colors: Yellow No. 4 (Tartrazine), Yellow No. 5 (Sunset Yellow FCF), Yellow No. 201 (Fluorescein), Yellow No. 202(1) (Uranine), Yellow No. 202 (2) (Uranine K), Yellow No. 203 (Quinoline Yellow) WS), Yellow No. 204 (Quinoline Yellow SS), Yellow No. 401 (Hanza Yellow), Yellow No. 403(1) (Naphthol Yellow S), Yellow No. 407 (Fast Light Yellow 3G), Iron Oxide Yellow (Hydrated Ferric Oxide), HC Yellow No. 7, HC Yellow No. 17, Basic Yellow No. 57, and red clay.

The red pigment may include the following colors or combination of the following colors: Red No. 2 (Amaranth), Red No. 40 (Allura Red AC), Red No. 102 (New Coccine), Red No. 103 (1) (Eosine YS), Red No. 104 (1) (Phloxine B), Red No. 104 (2) (Phloxine BK), Red No. 106 (Acid Red), Red No. 2 (Lithol Rubine B), Red No. 202 (Lithol Rubine BCA), Red No. 205 (Lithol Red), Red No. 206 (Lithol Red CA), Red No. 207 (Lithol Red BA), Red No. 208 (Lithol Red SR), Red No. 218 (Tetrachlorotetrabromofluorescein), Red No. 219 (Brilliant Lake Red R), Red No. 220 (Deep Maroon), Red No. 221 (Toluidine Red), Red No. 223 (Tetrabromofluorescein), Red No. 225 (Sudan III), Red No. 226 (Helindone Pink CN), Red No. 227 (Fast Acid Magenta), Red No. 228 (Permaton Red), Red No. 230 (2) (Eosine YSK), Red No. 401 (Violamine R), Red 405 (Permanent Red F5R), Red 504 (Ponceau SX), Red 506 (Fast Red S), Iron Oxide Red (Ferric Oxide), Basic Red 51, Basic Red 76 Basic Red 76, HC Red No. 1, Acid Red 52, and Acid Red 92.

The artificial tooth-forming material may have a viscosity between 300 and 800 cps (centipoise). "viscosity" refers to the viscosity measured at room temperature (25° C.) using Brookfield's DV-Rheometer RPM (shear rate: 25/s) in this specification.

The composition used to create artificial teeth may not include a solvent. However, the present invention is not restricted in this manner since the compound for creating artificial teeth may also contain a solvent.

The solvent may include the following substances or a combination of the following substances: ethanol, methanol, isopropanol, butanol, water, methylene glycol, ethylene glycol, propylene glycol, butylene glycol, neopentyl glycol, hexylene glycol, acetone, methyl ethyl ketone, ethyl acetate, butyl acetate, cyclohexanone, cyclohexane, methylene chloride, chloroform, carbon tetrachloride, trichloroethylene, perchloroethylene, methyl glycol acetate, toluene, benzene, diethyl ether, benzyl alcohol, and glycerin.

Further additives, such as a stabilizer and a plasticizer, may be added to the substance used to make artificial teeth.

The stabilizer may be comprised of benzophenone, oxanilide, benzotriazole, halogenated benzotriazole, triazine, or a mixture of these substances.

The plasticizer may consist of glycerin, propylene glycol, polyethylene glycol, ethylene glycol, sorbitol, mannitol, or a combination of these substances.

The artificial tooth-forming material may be liquid (or a suspension), photocurable, and 3D-printable.

The artificial tooth-forming composition may create a variety of natural tooth colors in humans according to the content ratio of each component within the range of 100 parts by weight of the total weight of the four photocurable compounds, 0.5 to 5 parts by weight of the acrylic resin, 1 to 20 parts by weight of the photoinitiator, 0.1 to 2 parts by weight of the antioxidant, 0.1 to 10 parts by weight of the white pigment and 0.001 to 0.15 parts by weight of the colored pigment. An opaque or translucent artificial tooth may be created. In other words, by appropriately adjusting the mixing ratio of the four photocurable compounds, the photoinitiator, the white pigment, and the colored pigment within the composition range of the composition for forming artificial teeth, an opaque or translucent artificial tooth with a color similar to the patient's natural tooth can be produced. Specifically, the color and/or opacity of the final artificial tooth may be determined by the mixing ratio of the four photocurable compounds, the acrylic resin, the antioxidant, the white pigment, and the colored pigment. In addition, the average particle diameter of the white pigment might affect the finished tooth's translucency.

Following is a detailed description of a technique for fabricating an artificial tooth in accordance with an embodiment of the present invention.

The method for producing artificial teeth according to one embodiment of the present invention is depicted in FIG. 1.

Referring to FIG. 1, a method for manufacturing artificial teeth according to one embodiment of the present invention comprises preparing a composition for forming artificial teeth (S10), manufacturing a partially cured artificial tooth by 3D printing the composition for forming an artificial tooth (S20), and fully hardening the partially cured artificial tooth to produce a final artificial tooth (S30).

In step (S10), the mixing ratios of the four photocurable compounds, the acrylic resin, the photoinitiator, the antioxidant, the white pigment, and the colored pigment may be adjusted appropriately within the composition range of the composition for forming artificial teeth to match the color of the patient's natural teeth.

In addition, the average particle diameter of the white pigment can be appropriately adjusted in step (S10) to prepare a composition for forming artificial teeth with high storage stability and/or composition for forming artificial teeth capable of producing opaque or translucent artificial teeth.

A 3D printer may carry out the step (S20). During the 3D printing process, the printed composition for producing artificial teeth is constantly or intermittently irradiated with UV radiation to partially cure the composition to create the artificial teeth. In this specification, "partial curing" refers to a cure rate between 40 and 90 percent.

In step (S30), the final artificial tooth is produced by fully curing the partially cured artificial tooth using a separate hardening device. In this standard, "complete curing" refers to a cure rate between 99 and 100 percent.

The following is a detailed description of artificial teeth produced using the production method for artificial teeth.

The artificial teeth offer superior aesthetics (color) and mechanical properties (high flexural strength and a suitable flexural modulus of elasticity).

The superior mechanical qualities of each photocurable compound are related to its physical properties and compounding ratio. The excellent aesthetics are the result of blending the photocurable compounds, the acrylic resin, the antioxidant, the white pigment, and the colored pigment in the proper proportions and managing the white pigment's particle size.

The following is a description of the current invention concerning the following examples. However, the present invention is not limited to these examples alone.

Implementation Examples 1-1 to 1-7 and Comparative Examples 1-1 to 1-6: Preparation of Compositions for Forming Artificial Teeth A composition for forming artificial teeth was prepared by using the following: diurethane dimethacrylate (Cas No. 72869-86-4, a mixture of R═H and R═CH3, molecular formula: C23H38N2O8) (PP1), which is a photocurable compound represented by Chemical Formula 1; bisphenol A glycerate dimethacrylate (Cas No. 1565-94-2) (PP2), represented by Chemical Formula 2; hydroxyethyl methacrylate (Cas No. 868-77-9)(PP3), represented by Chemical Formula 3; triethylene glycol dimethacrylate (Cas No. 109-16-0) (PP4), represented by Chemical Formula 4; dianal BR-8, which is an acrylic resin (manufactured by Mitsubishi Rayon, glass transition temperature 105° C., weighted average molecular weight 40,000); phenyl bis(2,4,6-trimethyl benzoyl)phosphine oxide, which is a photopolymerization initiator (Cas No. 162881-26-7); 2,4,6-di-tert-butyl-para-cresol, which is an antioxidant; rutile (Cas No. 1317-80-2) which is a white pigment; yellow pigment (custom-made from Wooshin Pigment) and an orange pigment. The orange pigment was prepared by combining a red pigment (custom-made from Wooshin Pigment) and a yellow pigment (custom-made from Wooshin Pigment) in a weight ratio of 2:8. Table 1 displays the materials and contents utilized in each Example and Comparative Example. The units for each numerical value in Table 1 are parts by weight. In addition, the quantities of acrylic resin, photoinitiator, antioxidant, white pigment, yellow pigment, and orange pigment are based on 100 parts by weight of the total weight of the four photopolymerizable compounds.

TABLE 1

| | | Implementation Examples | | | | | | |
|---|---|---|---|---|---|---|---|---|
| | | 1-1 | 1-2 | 1-3 | 1-4 | 1-5 | 1-6 | 1-7 |
| Photo-polymerizable compound | PP1 | 100 | 100 | 100 | 100 | 100 | 100 | 100 |
| | PP2 | 10 | 5 | 20 | 10 | 10 | 10 | 10 |
| | PP3 | 35 | 35 | 35 | 25 | 50 | 35 | 35 |
| | PP4 | 5 | 5 | 5 | 5 | 5 | 1 | 10 |
| Acrylic resin | | 2.5 | 2.5 | 2.5 | 2.5 | 2.5 | 2.5 | 2.5 |
| Photoinitiator | | 6 | 6 | 6 | 6 | 6 | 6 | 6 |
| Antioxidant | | 1 | 1 | 1 | 1 | 1 | 1 | 1 |
| White pigment | | 3 | 3 | 3 | 3 | 3 | 3 | 3 |
| Yellow pigment | | 0.03775 | 0.03775 | 0.03775 | 0.03775 | 0.03775 | 0.03775 | 0.03775 |
| Orange pigment | | 0.03775 | 0.03775 | 0.03775 | 0.03775 | 0.03775 | 0.03775 | 0.03775 |

| | | Comparative Examples | | | | | |
|---|---|---|---|---|---|---|---|
| | | 1-1 | 1-2 | 1-3 | 1-4 | 1-5 | 1-6 |
| Photo-polymerizable compound | PP1 | 100 | 100 | 100 | 100 | 100 | 100 |
| | PP2 | 3 | 25 | 10 | 10 | 10 | 10 |
| | PP3 | 35 | 35 | 20 | 55 | 35 | 35 |
| | PP4 | 5 | 5 | 5 | 5 | 0.5 | 15 |
| Acrylic resin | | 2.5 | 2.5 | 2.5 | 2.5 | 2.5 | 2.5 |
| Photoinitiator | | 6 | 6 | 6 | 6 | 6 | 6 |
| Antioxidant | | 1 | 1 | 1 | 1 | 1 | 1 |
| White pigment | | 3 | 3 | 3 | 3 | 3 | 3 |
| Yellow pigment | | 0.03775 | 0.03775 | 0.03775 | 0.03775 | 0.03775 | 0.03775 |
| Orange pigment | | 0.03775 | 0.03775 | 0.03775 | 0.03775 | 0.03775 | 0.03775 |

Implementation Examples 2-1 to 2-7 and Comparative Examples 2-1 to 2-6: Preparation of Compositions for Forming Artificial Teeth The compositions for forming artificial teeth created in each of the Implementation Examples and Comparative Examples were printed and partially cured using a 3D printer to produce partially cured artificial teeth. The partially cured artificial teeth were then completely cured using a hardening device to create final artificial teeth. The 3D printer and curing device are created together and are Ray Dent Studio products. Each artificial tooth-forming composition was used to create three artificial teeth.

Evaluation Example 1: Evaluation of Mechanical Properties of Artificial Teeth The flexural strength, the flexural modulus of elasticity (flexural calculation), and elongation at break were measured using a Material Testing Machine (MMS Company, Model: HZ-1004C, S/N: ABMMS14 5) for the artificial teeth manufactured in each of the above Examples and Comparative Examples and the findings are presented in Table 2 below.

Evaluation Example 2: Evaluation of Color and Transparency of Artificial Teeth The artificial teeth prepared in each of the preceding Implementation Examples and Comparative Examples were subjected to a sensory test. Specifically, the sensory test was administered in the following manner to five qualified evaluators: First, a Vita classical Shade guide including 16 distinct shades of colors was created. Each shade is made by replicating the natural tooth color of many individuals. Then, the artificial teeth created for Examples 2-1 to 2-7 and Comparative Examples 2-1 to 2-6 were compared to the Shade, and those with the closest color and transparency were matched one-to-one. Using a 5-point scale, the degree of color and transparency similarity between matched groups of artificial teeth and shades was then assessed, and the resulting scores were averaged and displayed in Table 2 below. The higher the score for each item, the higher the resemblance of the corresponding item.

TABLE 2

| | Implementation Examples | | | | | | |
|---|---|---|---|---|---|---|---|
| | 2-1 | 2-2 | 2-3 | 2-4 | 2-5 | 2-6 | 2-7 |
| Flexural strength (MPa) | 138 | 129 | 137 | 148 | 137 | 145 | 134 |
| Flexural modulus of elasticity (MPa) | 2445 | 2337 | 2267 | 2412 | 2429 | 2400 | 2446 |
| Color | 4.3 | 4.2 | 4.4 | 4.3 | 4.2 | 4.3 | 4.4 |
| Transparency | 3.0 | 2.8 | 2.7 | 2.9 | 2.6 | 2.7 | 2.8 |

| | Comparative Examples | | | | | |
|---|---|---|---|---|---|---|
| | 2-1 | 2-2 | 2-3 | 2-4 | 2-5 | 2-6 |
| Flexural strength (MPa) | 118 | 117 | 116 | 115 | 115 | 114 |
| Flexural modulus of elasticity (MPa) | 1732 | 2010 | 2017 | 1895 | 1875 | 1875 |
| Color | 4.4 | 4.3 | 4.3 | 4.3 | 4.4 | 4.3 |
| Transparency | 2.7 | 2.8 | 2.9 | 3.0 | 2.7 | 2.6 |

Referring to Table 2, the artificial teeth prepared according to Examples 2-1 to 2-7 exhibited greater flexural strength and flexural modulus of elasticity than the artificial teeth prepared according to Comparative Examples 2-1 to 2-6.

In addition, the artificial teeth prepared in Examples 2-1 to 2-7 and Comparative Examples 2-1 to 2-6 were comparable in color to each respective shade but were translucent because they had a low degree of transparency.

Although preferred implementations of the present invention have been discussed concerning the figures and examples provided above, other embodiments are possible. This is simply illustrative, and experts in the field will recognize that several variations and comparable implementations are feasible. Consequently, the extent of protection afforded by the present invention must be specified by the appended claims.

What is claimed is:

1. A composition for forming artificial teeth comprised of the following:

100 parts by weight of a first photocurable compound represented by Chemical Formula 1 below;

5 to 20 parts by weight of a second photocurable compound depicted by Chemical Formula 2 below;

25 to 50 parts by weight of a third photocurable compound represented by Chemical Formula 3 below;

1 to 10 parts by weight of the fourth photocurable compound by Chemical Formula 4; and 0.1 to 2 parts by weight of an antioxidant based on 100 parts by weight of the total weight of the first photocurable compound, the second photocurable compound, the third photocurable compound, and the fourth photocurable compound,

[Chemical Formula 1]

$$R'CH_2[C(CH_3)(R)CH_2]_2R'(R = H \text{ or } CH_3, R' {=\!=} NHCO_2CH_2CH_2O_2CC(CH_3){=\!=}CH_2)$$

[Chemical Formula 2]

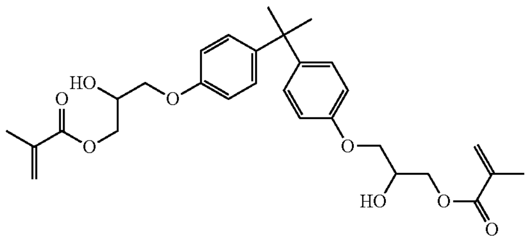

[Chemical Formula 3]

$$CH_2{=\!=}C(CH_3)COOCH_2CH_2OH$$

[Chemical Formula 4]

$$CH_2{=\!=}C(CH_3)COO(CH_2CH_2O)_3COC(CH_3){=\!=}CH_2.$$

2. The composition for forming artificial teeth of claim 1 which additionally includes 1 to 20 parts by weight of a photoinitiator based on 100 parts by weight of the total weight of the first photocurable compound, the second photocurable compound, the third photocurable compound, and the fourth photocurable compound.

3. The composition for forming artificial teeth of claim 1 that does not include a solvent.

4. The composition for forming artificial teeth of claim 1 with a viscosity of 300 to 800 cps.

5. The composition for forming artificial teeth of claim 1 which is in liquid state, photocurable, and used for 3D printing.

6. A method for manufacturing artificial teeth comprising steps of:

preparing the composition for forming artificial teeth according to claim 1 (S10);

manufacturing a partially cured artificial tooth by 3D printing the composition for creating artificial teeth (S20); and producing a final artificial teeth by completely curing the partially cured artificial teeth (S30).

7. An artificial tooth prepared using the method of producing artificial teeth of claim 6.

8. The artificial tooth of claim 7 which is an opaque or translucent artificial tooth.

9. A method for manufacturing artificial teeth comprising steps of:

preparing the composition for forming artificial teeth according to claim 3 (S10);

manufacturing a partially cured artificial tooth by 3D printing the composition for creating artificial teeth (S20); and producing a final artificial teeth by completely curing the partially cured artificial teeth (S30).

10. An artificial tooth prepared using the method of producing artificial teeth of claim 9.

11. The artificial tooth of claim 10 which is an opaque or translucent artificial tooth.

* * * * *